[54] SUBSTITUTED IMINODERIVATIVES OF DIHYDROBENZOPYRAN AND DIHYDROBENZOTHIOPYRAN

[75] Inventors: Lucio Merlini; Alessandro Rossi; Metilde Buonamici, all of Milan, Italy

[73] Assignee: Farmitalia Carlo Erba S.p.A., Milan, Italy

[21] Appl. No.: 491,386

[22] Filed: May 4, 1983

[30] Foreign Application Priority Data

May 6, 1982 [GB] United Kingdom ............... 8213109

[51] Int. Cl.$^3$ ............... A61K 31/35; A61K 31/38; C07D 311/68; C07D 335/06
[52] U.S. Cl. ............... 514/432; 514/443; 549/23; 549/345; 549/404
[58] Field of Search ............... 549/23, 345, 404; 424/275, 283

[56] References Cited

U.S. PATENT DOCUMENTS

| 3,467,676 | 9/1969 | Jen et al. ............... 549/401 |
| 3,507,885 | 4/1970 | Fahrenholtz ............... 549/390 |
| 3,636,058 | 1/1972 | Fahrenholtz ............... 549/280 |
| 4,003,915 | 1/1977 | Dostert et al. ............... 549/26 |
| 4,115,405 | 9/1978 | Wright et al. ............... 549/404 |
| 4,169,097 | 9/1979 | Wright et al. ............... 549/404 |

OTHER PUBLICATIONS

CA 95: 043031 (Merlini et al., J. Heterocycl. Chem., 81, 18, 23-25).
CA 90: 087677 (Luteyn et al., Recl. Trov. Chim. Pays--Bas, 78, 97 (7-8), 187-190).
CA 96: 068756 (Merlini et al., Heterocycles, 81, 16 (11), 1899-1900).
CA 68: 021778 (Fahrenholtz et al., J. Am. Chem. Soc., 67, 89 (23), 5934-5941).

Primary Examiner—Richard L. Raymond
Attorney, Agent, or Firm—Murray, Whisenhunt and Ferguson

[57] ABSTRACT

Substituted imino derivatives of 4 H-2, 3-dihydrobenzopyran and 4 H-2, 3-dihydrobenzothiopyran, and pharmaceutical compositions containing them. The compounds are active on the central nervous system, in particular as central nervous system depressants, i.e., sedatives, anticonvulsive agents, tranquilizers and sleep-inducing agents.

15 Claims, No Drawings

SUBSTITUTED IMINODERIVATIVES OF DIHYDROBENZOPYRAN AND DIHYDROBENZOTHIOPYRAN

The present invention relates to substituted iminoderivatives of 4H-2,3-dihydrobenzopyran and 4H-2,3-dihydrobenzothiopyran, to a process for their preparation and to pharmaceutical compositions containing them.

The invention provides compounds having the following general formula (I):

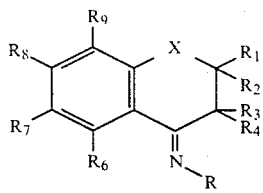

wherein
X is —O— or —S—;
each of $R_1$, $R_2$ and $R_3$, being the same or different, is hydrogen, $C_1$–$C_{10}$ alkyl or phenyl; or $R_1$ and $R_2$, taken together, form a $C_5$–$C_7$ cycloalkyl ring;
$R_4$ is hydrogen or $C_1$–$C_6$ alkyl;
$R_6$ is —$OR_{10}$ or —$SR_{10}$, wherein $R_{10}$ is hydrogen or $C_1$–$C_6$ alkyl;
$R_5$ is $C_1$–$C_{10}$ alkyl, $C_2$–$C_{10}$ alkenyl or $C_3$–$C_7$ cycloalkyl, wherein the alkyl, alkenyl and cycloalkyl groups are unsubstituted or substituted by one or more substituents chosen from the group consisting of halogen, oxo, —$OR_{10}$, —$SR_{10}$, —$COR_{10}$, —$OCOR_{10}$, —$COOR_{10}$ and

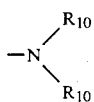

wherein each of the groups $R_{10}$, being the same or different, is as defined above;
one of $R_7$, $R_8$ and $R_9$ is $C_1$–$C_{12}$ alkyl and the others, which may be the same or different, are hydrogen or $C_1$–$C_{12}$ alkyl, and the pharmaceutically acceptable salts thereof.

The present invention includes all the possible isomers, comprising diastereoisomers, enantiomers and the mixtures thereof, of the compounds of the formula (I), as well as the metabolites and the metabolic precursors of the compounds of formula (I).

Pharmaceutically acceptable salts of the compounds of formula (I) include acid addition salts, with inorganic, e.g. nitric, hydrochloric, hydrobromic, sulphuric, perchloric and phosphoric, acids, or organic e.g. acetic, propionic, glycolic, lactic, oxalic, malonic, malic, maleic, tartaric, citric, benzoic, cinnamic, mandelic and salicyclic, acids, and salts with inorganic, e.g. alkali metal, especially sodium or potassium, bases or alkaline-earth metal, especially calcium or magnesium, bases, or with organic bases, e.g. alkylamines, preferably triethylamine.

The alkyl, alkoxy, alkenyl and alkylthio groups may be branched or straight chain groups.

A halogen atom is, for example, chlorine, bromine or fluorine; preferably it is chlorine. A di($C_1$–$C_6$)alkylamino group may be, for example, a di($C_1$–$C_4$ alkyl)amino, in particular a N-methyl-N-ethylamino, a N,N-dimethylamino or N,N-diethylamino group; preferably it is a N,N-dimethyl-amino or N,N-diethylamino group.

When one or more of $R_1$, $R_2$ and $R_3$ is $C_1$–$C_{10}$ alkyl, it is preferably $C_1$–$C_7$ alkyl, in particular methyl, ethyl, propyl, butyl, pentyl or hexyl.

When $R_1$ and $R_2$, taken together, form a $C_5$–$C_7$ cycloalkyl ring, it is preferably cyclopentyl or cyclohexyl.

When $R_5$ represents a $C_1$–$C_{10}$ alkyl group unsubstituted or substituted as defined above, it is preferably a branched or straight $C_1$–$C_5$ alkyl group, in particular a methyl, ethyl, propyl, butyl or pentyl group, substituted by one, two or three substituents chosen from the group consisting of oxo, —$OR'_{10}$, —$SR'_{10}$, —$COOR'_{10}$, —$OCOR'_{10}$ and

wherein each of the $R'_{10}$ groups, being the same or different is hydrogen or $C_1$–$C_4$ alkyl.

When $R_5$ represents a $C_3$–$C_7$ cycloalkyl group, optionally substituted as defined above, it is preferably chosen from cyclopropyl, cyclopentyl and cyclohexyl.

When $R_5$ is $C_2$–$C_{10}$ alkenyl, it is preferably $C_2$–$C_6$ alkenyl, in particular vinyl, 1-propenyl or allyl.

When the radical —$OR_{10}$ is $C_1$–$C_6$ alkoxy, it is preferably a $C_1$–$C_4$ alkoxy group, in particular methoxy, ethoxy, propoxy or isopropoxy.

When the radical —$SR_{10}$ is $C_1$–$C_6$ alkylthio, it is preferably a $C_1$–$C_4$ alkylthio group, in particular methylthio, ethylthio, propylthio or isopropylthio.

When the radical —$COR_{10}$ is a —$CO(C_1$–$C_6)$ alkyl group, it is preferably a —$CO(C_1$–$C_4)$ alkyl group, in particular acetyl, propionyl or butyryl.

When the radical —$OCOR_{10}$ is a —$OCO(C_1$–$C_6)$ alkyl group, it is preferably a $C_2$–$C_5$ alkanoyloxy group, in particular acetoxy, propionyloxy, butyryloxy or valeryloxy.

When the radical —$COOR_{10}$ is a —$COO(C_1$–$C_6)$ alkyl group, it is preferably a —$COO(C_1$–$C_4)$ alkyl group, in particular methoxycarbonyl, ethoxycarbonyl, propoxycarbonyl or isopropoxycarbonyl.

When $R_6$ represents a $C_1$–$C_6$ alkoxy group, it is preferably methoxy or ethoxy.

When $R_6$ represents a $C_1$–$C_6$ alkylthio group, it is preferably methylthio or ethylthio.

When one or more of $R_7$, $R_8$ and $R_9$ is $C_1$–$C_{12}$ alkyl, it is preferably $C_1$–$C_{10}$ alkyl, and more preferably methyl, propyl, butyl, tert-butyl, pentyl, hexyl, 1,1-dimethylheptyl or 1,2-dimethylheptyl.

Preferably, at least one of $R_7$, $R_8$ and $R_9$ is $C_4$–$C_{12}$ alkyl, more preferably $C_5$–$C_{10}$ alkyl, in particular pentyl.

Preferably X is —O—.

Preferred compounds of the invention are the compounds of formula (I), wherein
X is —O— or —S—;
$R_1$ is hydrogen, $C_1$–$C_7$ alkyl or phenyl;
$R_2$ is hydrogen or $C_1$–$C_4$ alkyl; or $R_1$ and $R_2$, taken together, form a $C_5$–$C_6$ cycloalkyl ring;
each of $R_3$ and $R_4$ is, independently, hydrogen or $C_1$–$C_4$ alkyl;
$R_5$ is $C_2$–$C_6$ alkenyl or $C_1$–$C_5$ alkyl, wherein the alkyl group is unsubstituted or substituted by one or two substituents chosen from oxo, —OR′$_{10}$, —SR′$_{10}$, —COOR′$_{10}$

and —OCOR′$_{10}$, wherein each of R′$_{10}$ is independently hydrogen or C$_1$–C$_4$ alkyl; or R$_5$ is C$_3$–C$_6$ cycloalkyl;

R$_6$ is hydroxy, mercapto, C$_1$–C$_2$ alkoxy or C$_1$–C$_2$ alkylthio; one of R$_7$, R$_8$ and R$_9$ is C$_4$–C$_{12}$ alkyl and the others, which may be the same or different, are hydrogen or C$_1$–C$_{12}$ alkyl, and the pharmaceutically acceptable salts thereof.

More preferred compounds of the invention are the compounds of formula (I), wherein X is —O— or —S—;

R$_1$ is hydrogen or C$_1$–C$_6$ alkyl; each of R$_2$, R$_3$ and R$_4$ is independently, hydrogen or C$_1$–C$_4$ alkyl;

R$_5$ is allyl, cyclopentyl, cyclohexyl or a radical chosen from 2-hydroxy-propyl-, 2-acetoxy-propyl-, 2-propionyloxy-propyl-, 2-hydroxy-ethyl-, 2-ethoxycarbonyl-ethyl-, 2-hydroxy-2-methyl-propyl-, 2-hydroxy-1-methyl-ethyl-, 2-hydroxy-butyl-, 1-hydroxymethyl-propyl-, 2-oxo-propyl-, 2-amino-propyl-, 2-dimethylamino-ethyl-, 2-methylamino-ethyl-, 2-mercapto-propyl-, 3-carboxy-propyl-, 2-methoxy-ethyl- and 2-mercapto-ethyl;

R$_6$ is hydroxy, mercapto, C$_1$–C$_2$ alkoxy or C$_1$–C$_2$ alkylthio; one of R$_7$, R$_8$ and R$_9$ is C$_5$–C$_{10}$ alkyl and the others are hydrogen, and the pharmaceutically acceptable salts thereof.

Examples of preferred compounds of the invention are:

2,2-dimethyl-5-hydroxy-7-(1′,2′-dimethylheptyl-4-(2′-hydroxypropylimino)-4H-2,3-dihydrobenzopyran;

2,2-dimethyl-5-hydroxy-7-pentyl-4-(2′-acetoxypropylimino)-4H-2,3-dihydrobenzopyran;

2,2-dimethyl-5-hydroxy-7-(1′,1′-dimethylheptyl)-4-(2′-hydroxypropylimino)-4H-2,3-dihydrobenzopyran;

2,2-dimethyl-5-hydroxy-7-pentyl-4-(2′-mercaptopropylimino)-4H-2,3-dihydrobenzopyran;

2,2-dimethyl-5-mercapto-7-pentyl-4-(2′-hydroxypropylimino)-4H-2,3-dihydrobenzopyran;

5-hydroxy-7-pentyl-4-(2′-hydroxypropylimino)-4H-2,3-dihydrobenzopyran;

2,2-dimethyl-5-hydroxy-7-pentyl-4-(2′-hydroxypropylimino)-4H-2,3-dihydrobenzothiopyran;

5-hydroxy-7-pentyl-4-(2′-hydroxypropylimino)-4H-2,3-dihydrobenzothiopyran;

2,2-dimethyl-5-hydroxy-7-pentyl-4-(2-dimethylaminoethylimino)-4H-2,3-dihydrobenzothiopyran; and 2,2-dimethyl-5-hydroxy-7-pentyl-4-allylimino-4H-2,3-dihydrobenzothiopyran;

and the pharmaceutically acceptable salts thereof.

Particularly preferred compounds of the invention are:

2,2-dimethyl-5-hydroxy-7-pentyl-4-(2′-hydroxypropylimino)-4H-2,3-dihydrobenzopyran;

(2′R)-2,2-dimethyl-5-hydroxy-7-pentyl-4-(2′-hydroxypropylimino)-4H-2,3-dihydrobenzopyran; and (2′S)-2,2-dimethyl-5-hydroxy-7-pentyl-4-(2′-hydroxypropylimino)-4H-2,3-dihydrobenzopyran;

and the pharmaceutically acceptable salts thereof.

The compounds of formula (I) can be obtained by a process comprising reacting a compound of formula (II)

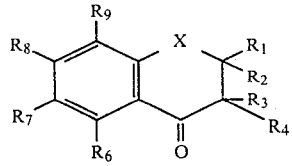

wherein

X, R$_1$, R$_2$, R$_3$, R$_4$, R$_6$, R$_7$, R$_8$ and R$_9$ are as defined above, or a salt thereof, with an amine of formula (III)

$$H_2N-R_5 \qquad (III)$$

wherein

R$_5$ is as defined above, or a salt thereof; and, if desired, converting a compound of formula (I) into another compound of formula (I) and/or, if desired, converting a compound of formula (I) into a pharmaceutically acceptable salt thereof and/or, if desired, converting a salt into a free compound and/or, if desired, separating a mixture of isomers into the single isomers.

The reaction of a compound of formula (II) or a salt thereof with an amine of formula (III) or a salt thereof is, preferably, carried out in the presence of a base, for example, triethylamine, sodium carbonate, or diazabicycloundecene, preferably triethylamine, in an organic solvent chosen, for example, from a C$_1$–C$_6$ aliphatic alcohol, preferably methanol or ethanol, or from an aromatic hydrocarbon, preferably benzene or toluene, or from ethers, preferably dioxane, or from nitriles, preferably acetonitrile, at a temperature ranging between about 25° C. and the reflux temperature of the solvent used, preferably between about 70° C. and about 120° C., with or without distillation of solvent to remove the water formed during the reaction, with or without the presence of a dehydrating agent, for example, sodium sulphate or magnesium sulphate, or molecular seives, with or without the presence of a catalyst, for example, TiCl$_4$ or ZnCl$_2$ or others, for example, those reported by I. Moretti and G. Torre, in Synthesis, 1970, page 141, for these kinds of reactions. A compound of formula (I) may be converted, as stated above, into another compound of formula (I) by known methods. For example, a free hydroxy or thiol group may be etherified by reaction with a suitable alkyl halide in the presence of a base such as NaOH, KOH, Na$_2$CO$_3$, K$_2$CO$_3$, NaH, NaNH$_2$, sodium methoxide or sodium ethoxide in a solvent selected from the group consisting, for example, of methanol, ethanol, dioxane, acetone, dimethylformamide, hexamethylphosphorotriamide, tetrahydrofuran, water and their mixtures at a temperature ranging preferably between about 0° C. and about 150° C. Furthermore an etherified hydroxy group may be converted into a free hydroxy group, for example, by treatment with pyridine hydrochloride or with a strong acid such as HBr or HI, or with a Lewis acid such as AlCl$_3$ or BBr$_3$ or with an alkaline salt of a thiol.

An esterified carboxy group may be converted into a free carboxy group by hydrolysis, e.g. basic hydrolysis, using, for example, sodium or potassium hydroxide, in a solvent such as water or a lower aliphatic alcohol, and operating at a temperature ranging from the room temperature to about 150° C.; the same reaction may be also carried out e.g. by treatment with lithium bromide in dimethylformamide at a temperature higher than 50° C.

A unesterified carboxy group may be converted into an esterified carboxy group by conventional methods, for example, by reacting a salt, e.g. an alkali metal salt, of the acid with a suitable alkyl halide in an inert solvent, such as acetone dioxane, dimethylformamide or hexamethylphosphorotriamide at a temperature ranging from 0° C. to about 100° C.

Alternatively said esterification may effected (a) by converting the carboxylic acid into the corresponding halocarbonyl, preferably chlorocarbonyl, derivative, by reaction, e.g. with the desired acid halide, for example oxalyl chloride, thionyl chloride, $PCl_3$, $PCl_5$ or $POCl_3$, either in the absence of solvents, or in an inert organic solvent such as benzene, toluene, xylene, dioxane, dichloroethane, methylene chloride or tetrahydrofuran, at a temperature ranging preferably from about 0° C. to about 120° C.; and then (b) reacting the resulting halocarbonyl derivative with the suitable alcohol of formula $R_{10}$—OH, wherein $R_{10}$ is a $C_1$–$C_6$ alkyl group, in an inert solvent such as benzene, toluene, xylene, dioxane, dichloroethane, methylene chloride or tetrahydrofuran, at temperatures varying between about 0° C. and about 120° C., preferably in the presence of a base, such as, triethylamine or diethylamine.

A free hydroxy group may be esterified, thus obtaining a —$OCOR_{10}$ group, wherein $R_{10}$ is as defined above, according to known methods. For example a free hydroxy group may be converted into an alkanoyloxy group by treatment with a suitable acylating agent, e.g., a reactive derivative of a suitable saturated aliphatic carboxylic acid, such as an anhydride or an halide, preferably the chloride, thereof and in the presence of a basic agent, preferably an organic base, such as pyridine. The reaction may be carried out at a temperature ranging from about room temperature to about 100° C.

A free hydroxy group may be oxidized to the corresponding oxo group by a suitable oxidizing agent, such as for example pyridine-$CrO_3$ or pyridine-chloro chromate or manganese dioxide.

When required, reactive functional groups may be protected with suitable protecting reagents, which may be removed after the reaction by known methods, which are available from the chemical literature.

Also the optional salification of a compound of formula (I) as well the conversion of a salt into the free compound and the separation of a mixture of isomers into the single isomers may be carried out by conventional methods.

For example the separation of a mixture of optical isomers into the individual isomers may be carried out by salification with an optically active acid and subsequent fractional crystallization or by esterification with an optically active acid derivative and separation of the diastereoisomers.

Thus, the separation of a mixture of geometric isomers may be carried out, for example, by fractional crystallization or by separation on column chromatography.

The compounds of formula (II), wherein X is —O—, may be prepared, for example, by reacting a compound of formula (IV)

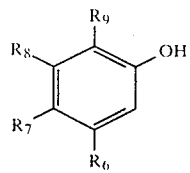

wherein $R_6$, $R_7$, $R_8$ and $R_9$ are as defined above or a salt thereof, with a compound of formula (V)

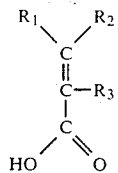

wherein $R_1$, $R_2$ and $R_3$ are as defined above, or a reactive derivative thereof, so obtaining a compound of formula (II), wherein $R_1$, $R_2$, $R_3$, $R_6$, $R_7$, $R_8$ and $R_9$ are as defined above, X is —O— and $R_4$ is hydrogen.

A reactive derivative of a compound of formula (V) is for example, an acyl halide, an anhydride, a mixed anhydride, an azide, a reactive ester. A reactive ester may be, for example, a p-nitrophenyl ester, a 2,4-dinitrophenyl ester, a pentachlorophenyl ester, a N-hydroxysuccinimide ester or a N-hydroxyphthalimide ester.

The reaction between a compound of formula (IV), or a salt thereof, and a compound of formula (V), or a reactive derivative thereof, may be carried out by following known procedures for this kind of reaction, for example, in the presence of an acid or a Lewis acid catalyst, e.g. boron trifluoride etherate, or $AlCl_3$, without a solvent or in a solvent, preferably chosen from diethyl ether or carbon disulphide or nitrobenzene, at a temperature ranging from about 30° C. to about 180° C.; or according to the procedures reported in "Chromenes, Chromanones, Chromones", G. P. Ellis ed. Wiley Interscience, New York 1977.

The compounds of formula (II), wherein X is —S—, may be obtained by following analogous processes known in the literature, for example by cyclodehydration of a compound of formula (VI)

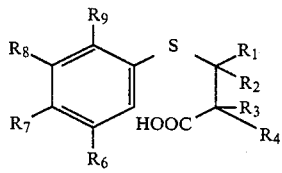

wherein $R_1$, $R_2$, $R_3$, $R_4$, $R_6$, $R_7$, $R_8$ and $R_9$ are as defined above, or a reactive derivative thereof.

A reactive derivative of a compound of formula (VI) may be for example an acyl chloride an anhydride, a mixed anhydride or reactive ester.

The cyclodehydration of a compound of formula (VI) may be carried out, for example, by treatment with a strong mineral acid, e.g. with concentrated sulphuric acid, preferably at temperatures between 25° C. and 60° C. or with excess of polyphosphoric acid, or with hydrogen fluoride, or in the presence of Lewis acids, such as $BF_3$, $AlCl_3$, $SnCl_4$ without a solvent or in a solvent, e.g., diethyl ether, methylene chloride, or nitrobenzene.

Furthermore the compounds of formula (II), wherein X is —S—, may be prepared according to other procedures reported in the literature, for example by cycloaddition onto a o-methylenethioquinone, or such as those given by J. W. Schneller in "Advances in Heterocyclic Chemistry", vol. 18, Academic Press, New York. 1975.

If desired a compound of formula (II) or a salt thereof may be converted into another compound of formula (II), or a salt thereof.

For example, a compound of formula (II), wherein $R_4$ is hydrogen, may be converted into another compound of formula (II), wherein $R_4$ is $C_1-C_6$ alkyl, by following an alkylation process. The alkylation of a compound of formula (II) may be carried out, for example, by reaction with NaH or $NaNH_2$ in dry dioxane, or dimethylformamide, or toluene, and alkylating the obtained anion with an alkyl sulphate.

A compound of formula (II) wherein $R_6$ is hydroxy may be converted into another compound of formula (II) wherein $R_6$ is a $C_1-C_6$ alkoxy group by alkylation, for example, with alkyl sulfates or halides, e.g. by reaction with an alkyl iodide in dry acetone in the presence of excess sodium carbonate, or by reaction with an alkyl iodide and silver oxide in dimethylformamide at room temperature.

Furthermore a compound of formula (II), wherein $R_6$ is hydroxy may be converted into another compound of formula (II) wherein $R_6$ is a —SH group, by following known methods, for example, according to the procedure of H. Wolfers, U. Kraatz, F. Korte, Synthesis, 1971, page 43.

The compounds of formula (III), (IV), (V) and (VI) either are compounds reported in the literature, or may be prepared according to known methods. The compounds of the invention are active on the central nervous system (CNS), in particular as central nervous system depressants, i.e. as sedative, anticonvulsive agents, minor tranquilizers, and as sleep-inducing agents. The activity on the CNS of the compounds of the invention was evaluated, for example, in the experimental framework of the behavioural assessment by the Irwin's technique [Irwin, S., Psychopharmacologia (Berl.), 13, 222, 1968]. In this test, the compounds of the invention, for example 2,2-dimethyl-5-hydroxy-7-pentyl-4-(2'-hydroxypropylimino)-4H-2,3-dihydrobenzopyran and (2'R)-2,2-dimethyl-5-hydroxy-7-pentyl-4-(2'-hydroxypropylimino)-4H-2,3-dihydrobenzopyran proved to be very active as CNS depressants, in particular as sedative agents and as minor tranquilizers, and in inducing hypnosis e.g. in mice and rats. The animals, treated with oral doses ranging from 5 to 100 mg/kg body weight, showed loss of righting reflex, without contemporary depression of muscle-tone, respiratory frequency, rectal temperature and of other less indicative reflexes.

The compounds of the invention, for example the above-mentioned 2,2-dimethyl-5-hydroxy-7-pentyl-4-(2'-hydroxypropylimino)-4H-2,3-dihydrobenzopyran and (2'R)-2,2-dimethyl-5-hydroxy-7-pentyl-4-(2'-hydroxypropylimino)-4H-2,3-dihydrobenzopyran, were also, orally tested to evaluate their effects on the sleep-waking cycle of the rat [Loew, D. M. and Spiegel, R., Arzneim.-Forsch. (Drug Res.) 26 (6): 1032, 1976] and they increased the duration of slow wave sleep, but leaving the Paradoxical Sleep time (REM sleep) unaffected.

The anticonvulsive activity of the compounds of the invention, e.g. 2,2-dimethyl-5-hydroxy-7-pentyl-4-(2'-hydroxypropylimino)-4H-2,3-dihydrobenzoypyran and (2'R)-2,2-dimethyl-5-hydroxy-7-pentyl-4-(2'-hydroxypropylimino)-4H-2,3-dihydrobenzopyran, was evaluated for example in mice by the inhibition of pentylenetetrazole-induced maximal seizures. Pentylenetetrazole was administered 30 minutes after the oral screening dose of the compounds at the i.p. dose of 130 mg/kg.

The toxicity of the compounds of the invention is negligible, therefore they can be safely used in therapy. Nine hours food deprived mice and rats were treated orally with single administration of increasing doses, then housed and normally fed. The orientative acute toxicity ($LD_{50}$) was assessed on the seventh day after the treatment and resulted, in general, higher than 600 mg/kg.

The compounds of the invention can be administered in a variety of dosage forms, e.g. orally, in the form of tablets, capsules, sugar or film coated tablets, liquid solutions or suspensions, rectally, in the form of suppositories, parenterally, e.g. intramuscularly, or by intravenous injection or infusion. The dosage depends on the age, weight, conditions of the patient and administration route; for example the dosage adopted for oral administration to adult humans ranges from about 5 to about 100 mg pro dose, from 1 to 5 times daily.

The invention includes pharmaceutical compositions comprising a compound of the invention in association with a pharmaceutically acceptable excipient (which can be a carrier or diluent).

The pharmaceutical compositions containing the compounds of the invention are usually prepared following conventional methods and are administered in a pharmaceutically suitable form.

For example, the solid oral forms may contain, together with the active compound, diluents, e.g., lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

The liquid dispersions for oral administration may be e.g. syrups, emulsions and suspensions. The syrups may contain as carriers for example, saccharose or saccharose with glycerine and/or mannitol and/or sorbitol; in particular a syrup to be administered to diabetic patients can contain as carriers only products not metabolizable to glucose, or metabolizable in very small amount to glucose, for example sorbitol.

The suspensions and the emulsions may contain as carrier, for example, a natural gum, agar, sodium alginate, pectin, methylcellulose, carboxymethylcellulose, or polyvinyl alcohol. The suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

The solutions for intravenous injections or infusions may contain as carrier, for example, sterile water or preferably they may be in the form of sterile, aqueous, isotonic saline solutions.

The suppositories may contain, together with the active compound, a pharmaceutically acceptable carrier, e.g. cocoa-butter, polyethylene glycol, a polyoxyethylene sorbitan fatty acid ester surfactant or lecithin.

The following examples illustrate but do not limit the invention.

EXAMPLE 1

A solution of 5 g of 2,2-dimethyl-5-hydroxy-7-pentyl-4H-2,3-dihydrobenzopyran-4-one and of 4 g of 1-amino-2-propanol in 50 ml of ethanol was refluxed 20 hrs. The solvent was evaporated in vacuo, the residue taken up with water and ethyl acetate, the aqueous layer further extracted with ethyl acetate, the extracts combined and repeatedly washed with water, dried with anhydrous Na₂SO₄ filtered and evaporated, the residue taken up with ether, cooled at −5° C., the crystallized product filtered, to give 3.1 g of 2,2-dimethyl-5-hydroxy-7-pentyl-4-(2′-hydroxypropylimino)-4H-2,3-dihydrobenzopyran, as a yellow solid, m.p. 90°–92° C. A further crop of 0.4 g of the product was obtained by subjecting the mother liquors of the crystallization to flash chromatography on silica gel Merck 60 with a mixture of hexane and ethyl acetate 1/1 as eluent.

The following compounds as pure enantiomers and as a racemic mixture thereof were analogously prepared:
2,2-dimethyl-5-hydroxy-7-pentyl-4-(2′-hydroxy-1′-methyl-ethylimino)-4H-2,3-dihydrobenzopyran, m.p. 67°–69° C.;
2,2-dimethyl-5-hydroxy-7-pentyl-4-(4′-hydroxybutylimino)-4H-2,3-dihydrobenzopyran, m.p. 112°–113° C.;
2,2-dimethyl-5-hydroxy-7-pentyl-4-(3′-hydroxypropylimino)-4H-2,3-dihydrobenzopyran, m.p. 83°–86° C.;
2,2-dimethyl-5-hydroxy-7-(1′,2′-dimethylheptyl)-4-(2′-hydroxypropylimino)-4H-2,3-dihydrobenzopyran;
2,2-dimethyl-5-hydroxy-7-pentyl-4-(2′-mercaptopropylimino)-4H-2,3-dihydrobenzopyran;
5-hydroxy-7-pentyl-4-(2′-hydroxypropylimino)-4H-2,3-dihydrobenzopyran;
2-methyl-B 5-hydroxy-7-pentyl-4-(2′-hydroxypropylimino)-4H-2,3-dihydrobenzopyran;
2-phenyl-5-hydroxy-7-pentyl-4-(2′-hydroxypropylimino)-4H-2,3-dihydrobenzopyran;
2,2-dimethyl-5-hydroxy-7-propyl-4-(2′-hydroxypropylimino)-4H-2,3-dihydrobenzopyran;
2,2-dimethyl-5-hydroxy-7-butyl-4-(2′-hydroxypropylimino)-4H-2,3-dihydrobenzopyran;
2,2-dimethyl-5-hydroxy-7-pentyl-4-(2′-aminopropylimino)-4H-2,3-dihydrobenzopyran;
2,2-dimethyl-5-hydroxy-7-pentyl-4-(2′-dimethylaminoethylimino)-4H-2,3-dihydrobenzopyran;
2,2-dimethyl-5-hydroxy-7-pentyl-4-cyclopropylimino-4H-2,3-dihydrobenzopyran;
2,2-dimethyl-5-hydroxy-7-pentyl-4-(2′-oxopropylimino)-4H-2,3-dihydrobenzopyran;
2,2-dimethyl-5-hydroxy-7-pentyl-4-(2′-ethoxycarbonylethylimino)-4H-2,3-dihydrobenzopyran;
2,2-dimethyl-5-hydroxy-7-pentyl-4-(2′-hydroxy-2′-methylpropylimino)-4H-2,3-dihydrobenzopyran;
2,2-dimethyl-5-hydroxy-7-pentyl-4-(2′-hydroxybutylimino)-4H-2,3-dihydrobenzopyran;
2,2-dimethyl-5-hydroxy-7-hexyl-4-(2′-hydroxypropylimino)-4H-2,3-dihydrobenzopyran;
2,7-dipentyl-5-hydroxy-4-(2′-hydroxypropylimino)-4H-2,3-dihydrobenzopyran;
2,2-dimethyl-5-hydroxy-7-(1′,1′-dimethylheptyl)-4-(2′-hydroxypropylimino)-4H-2,3-dihydrobenzopyran;
2,2-dimethyl-5-hydroxy-7-pentyl-4-(2′,3′-dihydroxypropylimino)-4H-2,3-dihydrobenzopyran, m.p. 127°–129° C.;
2-methyl-5-hydroxy-7-(1′,1′-dimethylheptyl)-4-(2′-hydroxypropylimino)-4H-2,3-dihydrobenzopyran;
5-hydroxy-7-(1′,1′-dimethylheptyl)-4-(2′-hydroxypropylimino)-4H-2,3-dihydrobenzopyran;
2-methyl-5-hydroxy-7-(1′,2′-dimethylheptyl)-4-(2′-hydroxypropylimino)-4H-2,3-dihydrobenzopyran;
5-hydroxy-7-(1′,2′-dimethylheptyl)-4-(2′-hydroxypropylimino)-4H-2,3-dihydrobenzopyran;
2,2-dimethyl-5-mercapto-7-pentyl-4-(2′-hydroxypropylimino)-4H-2,3-dihydrobenzopyran;
2-methyl-5-mercapto-7-pentyl-4-(2′-hydroxypropylimino)-4H-2,3-dihydrobenzopyran;
2,2-dimethyl-5-mercapto-7-(1′,2′-dimethylheptyl)-4-(2′-hydroxypropylimino)-4H-2,3-dihydrobenzopyran;
2,2-dimethyl-5-mercapto-7-(1′,1′-dimethylheptyl)-4-(2′-hydroxypropylimino)-4H-2,3-dihydrobenzopyran
and
2-pentyl-5-hydroxy-7-methyl-4-(2′-hydroxypropylimino)-4H-2,3-dihydrobenzopyran, m.p. 112°–114° C.

EXAMPLE 2

By proceeding according to Example 1 and using as starting material the (2′R)- and the (2′S)-enantiomer of the compound 1-amino-2-propanol, the following compounds were respectively obtained:
(2′R)-2,2-dimethyl-5-hydroxy-7-pentyl-4-(2′-hydroxypropylimino)-4H-2,3-dihydrobenzopyran, m.p. 102°–104° C., $[\alpha]_D^{20} = -25.74$ (Et OH, c 0.093); and
(2′S)-2,2-dimethyl-5-hydroxy-7-pentyl-4-(2′-hydroxypropylimino)-4H-2,3-dihydrobenzopyran, m.p. 102°–104° C., $[\alpha]_D^{20} = +26.24$ (Et OH, c 0.09).

EXAMPLE 3

A solution of 3 g of 2,2-dimethyl-5-hydroxy-7-pentyl-4H-2,3-dihydrobenzopyran-4-one and of 3 g of 2-aminoethanol in 80 ml of toluene was refluxed 20 hrs. in a Soxhlet extractor with a thimble containing 3 Å molecular sieves. The yellow solution was evaporated in vacuo, and the residue crystallized from ethanol to give 2.8 g of 2,2-dimethyl-5-hydroxy-7-pentyl-4-(2′-hydroxyethylimino)-4H-2,3-dihydrobenzopyran, m.p. 108°–110° C.

The following compounds as pure enantiomers and as racemic mixture thereof were analogously prepared:
2,2-dimethyl-5-hydroxy-7-pentyl-4-(2′-methoxyethylimino)-4H-2,3-dihydrobenzopyran, oil, b.p. 190° C./1 mm Hg;
2,2,7-trimethyl-5-hydroxy-4-(2′-hydroxypropylimino)-4H-2,3-dihydrobenzopyran, m.p. 157°–158° C.;
2,2-dimethyl-5-hydroxy-7-pentyl-4-(2′-mercaptoethylimino)-4H-2,3-dihydrobenzopyran, m.p. 91°–93° C.;
2-methyl-5-hydroxy-6-hexyl-4-(2′-hydroxypropylimino)-4H-2,3-dihydrobenzopyran;
2,2-dimethyl-5-hydroxy-7-pentyl-4-dimethylaminomethylimino-4H-2,3-dihydrobenzopyran;
2,2-dimethyl-5-hydroxy-7-pentyl-4-(2′-ethoxycarbonylethylimino)-4H-2,3-dihydrobenzopyran;

2,2-dimethyl-5-hydroxy-7-pentyl-4-(3'-carboxy-
propylimino)-4H-2,3-dihydrobenzopyran;
2,2-dimethyl-5-mercapto-7-pentyl-4-(2'-hydroxye-
thylimino)-4H-2,3-dihydrobenzopyran; and
2,2-dimethyl-5-hydroxy-7-pentyl-4-(2'-hydroxyhep-
tylimino)-4H-2,3-dihydrobenzopyran.

EXAMPLE 4

A solution of 2.62 g (0.01 mol) of 2,2-dimethyl-5-hydroxy-7-pentyl-4H-2,3-dihydrobenzopyran-4-one and of 5 g of cyclohexylamine in 500 ml of dry benzene was cooled at −5° C., and added dropwise with a solution of 0.006 mol of TiCl$_4$ in 20 ml of dry benzene. After the addition was complete, the mixture was stirred for 24 hrs., filtered, the solvent was evaporated, the residue taken up with chloroform and water, the chloroform layer washed with water, dried with Na$_2$SO$_4$, the solvent evaporated and the residue chromatographed on silica gel with hexane; ethyl acetate=1:1 v/v as eluent, to give 1.85 of 2,2-dimethyl-5-hydroxy-7-pentyl-4-cyclohexylimino-4H-2,3-dihydrobenzopyran, as a low melting solid.

The following compounds as pure enatiomers and as racemic mixture thereof were analogously prepared:
2,2-dimethyl-5-hydroxy-7-pentyl-4-(1'-hydroxy-2'-
butyl-imino)-4H-2,3-dihydrobenzopyran, m.p. 79°–80° C.;
3-phenyl-5-hydroxy-7-pentyl-4-(2'-hydroxy-
propylimino)-4H-2,3-dihydrobenzopyran;
cyclopentan(spiro-2)-5-hydroxy-7-methyl-4-(2'-hydrox-
ypropylimino)-4H-2,3-dihydrobenzopyran;
2,2-dimethyl-5-hydroxy-7-pentyl-4-(2'-methylaminoe-
thylimino)-4H-2,3-dihydrobenzopyran;
2,2-dimethyl-5-hydroxy-7-pentyl-4-allylimino-4H-2,3-
dihydrobenzopyran, m.p. 69°–70° C.;
2,2-dimethyl-5-hydroxy-7-(1',1'-dimethylethyl)-4-(2'-
hydroxypropylimino)-4H-2,3-dihydrobenzopyran; and
2,7-dipentyl-5-mercapto-4-(2'-hydroxypropylimino)-
4H-2,3-dihydrobenzopyran.

EXAMPLE 5

300 mg of (2'R)-2,2-dimethyl-5-hydroxy-7-pentyl-4-(2'-hydroxypropylimino)-4H-2,3-dihydrobenzopyran were suspended in 5 ml of 0.5N hydrochloric acid and stirred 0.5 hrs. Filtration and washing with diluted HCl gave 305 mg of (2'R)-2,2-dimethyl-5-hydroxy-7-pentyl-4-(2'-hydroxypropylimino)-4H-2,3-dihydrobenzopyran hydrochloride, m.p. 159°–161° C.

The following compounds were analogously prepared:
2,2-dimethyl-5-hydroxy-7-pentyl-4-(3'-hydroxy-
propylimino)-4H-2,3-dihydrobenzopyran hydrochloride, m.p. 172°–174° C.; and
2,2-dimethyl-5-hydroxy-7-pentyl-4-cyclohexylimino-
4H-2,3-dihydrobenzopyran hydrochloride, m.p. 195°–198° C.

EXAMPLE 6

2.7 g of 2,2-dimethyl-5-hydroxy-7-pentyl-4H-2,3-dihydrobenzothiopyran-4-one and 2 g of 2-aminoethanol in 20 ml of ethanol were refluxed 15 hrs. The mixture was cooled, evaporated, taken up with water, extracted with chloroform. The chloroform solution was repeatedly washed with water, dried with Na$_2$SO$_4$ and evaporated to give 1.5 g of 2,2-dimethyl-5-hydroxy-7-pentyl-4-(2'-hydroxyethylimino)-4H-2,3-dihydrobenzothiopyran, as a glassy solid.

The following compounds, as pure enantiomers and as a racemic mixture thereof, were analogously prepared:
5-hydroxy-7-pentyl-4-(2'-hydroxypropylimino)-4H-2,3-
dihydrobenzothiopyran;
2,2-dimethyl-5-hydroxy-6-hexyl-4-(2'-hydroxy-
propylimino)-4H-2,3-dihydrobenzothiopyran;
2,2,7-trimethyl-5-hydroxy-4-(2'-hydroxypropylimino)-
4H-2,3-dihydrobenzothiopyran;
2,2-dimethyl-5-hydroxy-7-pentyl-4-(2'-hydroxy-
propylimino)-4H-2,3-dihydrobenzothiopyran.
2-methyl-5-hydroxy-7-pentyl-4-(2'-hydroxy-
propylimino)-4H-2,3-dihydrobenzothiopyran;
2,2-dimethyl-5-hydroxy-7-(1',2'-dimethylheptyl)-4-(2'-
hydroxyethylimino)-4H-2,3-dihydrobenzothiopyran;
2,2-dimethyl-5-hydroxy-7-pentyl-4-cyclopropylimino-
4H-2,3-dihydrobenzothiopyran;
2-phenyl-5-hydroxy-7-methyl-4-(2'-hydroxy-
propylimino)-4H-2,3-dihydrobenzothiopyran;
2,2-dimethyl-7-propyl-5-hydroxy-4-(2'-hydroxy-
propylimino)-4H-2,3-dihydrobenzothiopyran;
2,2-dimethyl-5-hydroxy-7-pentyl-4-(2'-dimethylaminoe-
thylimino)-4H-2,3-dihydrobenzothiopyran;
2,2-dimethyl-5-hydroxy-7-pentyl-4-(2'-mercapto-
propylimino)-4H-2,3-dihydrobenzothiopyran;
2,2-dimethyl-5-hydroxy-7-pentyl-4-(3'-carboxy-
propylimino)-4H-2,3-dihydrobenzothiopyran;
2,2-dimethyl-5-hydroxy-7-pentyl-4-(2'-ethoxycar-
bonylethylimino)-4H-2,3-dihydrobenzothiopyran;
2,2-dimethyl-5-hydroxy-7-pentyl-4-allylimino-4H-2,3-
dihydrobenzothiopyran;
2-methyl-5-hydroxy-7-pentyl-4-(2'-hydroxye-
thylimino)-4H-2,3-dihydrobenzothiopyran;
2,2-dimethyl-5-hydroxy-7-pentyl-4-(2'-hydrox-
ybutylimino)-4H-2,3-dihydrobenzothiopyran;
2,2-dimethyl-5-hydroxy-7-(1',2'-dimethylheptyl)-4-(2'-
hydroxypropylimino)-4H-2,3-dihydrobenzothiopyran;
2,2-dimethyl-5-hydroxy-7-(1',1'-dimethylheptyl)-4-(2'-
hydroxypropylimino)-4H-2,3-dihydrobenzothiopyran; and
5-hydroxy-7-pentyl-4-(2'-hydroxybutylimino)-4H-2,3-
dihydrobenzothiopyran.

EXAMPLE 7

By proceeding according to Example 6 and using as starting material the (2'R)- and the (2'S)-enantiomer of the compound 1-amino-2-propanol, the following compounds were respectively obtained:
(2'R)-2,2-dimethyl-5-hydroxy-7-pentyl-4-(2'-hydroxy-
propylimino)-4H-2,3-dihydrobenzothiopyran; and
(2'S)-2,2-dimethyl-5-hydroxy-7-pentyl-4-(2'-hydroxy-
propylimino)4H-2,3-dihydrobenzothiopyran;

EXAMPLE 8

To a solution of 321 mg (0.001 mol) of 2,2,7-trimethyl-5-hydroxy-4-(2'-hydroxypropylimino)-4H-2,3-dihydrobenzothiopyran in 1 ml of pyridine 3 ml of acetic anhydride were added, and the mixture heated for half an hour.

The solvents were evaporated in vacuo, the residue taken up with water and ethyl acetate, the organic layer washed with 5% aqueous NaHCO$_3$, then with water, dried with Na$_2$SO$_4$, and evaporated to give a crude product which was chromatographed on silica gel with hexane:ethyl acetate=7:3 v/v as eluent to give 273 mg of 2,2,7-trimethyl-5-hydroxy-4-(2'-acetoxypropylimino)-4H-2,3-dihydrobenzothiopyran, as a glassy solid.

The following compounds as pure enantiomers and as a racemic mixture thereof were analogously prepared:
2,2,7-trimethyl-5-hydroxy-4-(2'acetoxypropylimino)-4H-2,3-dihydrobenzopyran;
2,2-dimethyl-5-hydroxy-7-pentyl-4-(2'-acetoxypropylimino)-4H-2,3-dihydrobenzopyran;
2,2-dimethyl-5-hydroxy-7-pentyl-4-(2'-propionyloxypropylimino)-4H-2,3-dihydrobenzopyran;
2,2-dimethyl-5-hydroxy-7-pentyl-4-(2'-acetoxypropylimino)-4H-2,3-dihydrobenzothiopyran.

EXAMPLE 9

By proceeding according to Example 8 and using as starting material the (2'R)- and the (2'S)-enantiomers of the compounds 2,2-dimethyl-5-hydroxy-7-pentyl-4-(2'-hydroxypropylimino)-4H-2,3-dihydrobenzopyran and 2,2-dimethyl-5-hydroxy-7-pentyl-4-(2'-hydroxypropylimino)-4H-2,3-dihydrobenzothiopyran, the following compounds were respectively obtained:
(2'R)-2,2-dimethyl-5-hydroxy-7-pentyl-4-(2'-acetoxypropylimino)-4H-2,3-dihydrobenzopyran;
(2'S)-2,2-dimethyl-5-hydroxy-7-pentyl-4-(2'-acetoxypropylimino)-4H-2,3-dihydrobenzopyran;
(2'R)-2,2-dimethyl-5-hydroxy-7-pentyl-4-(2'-acetoxypropylimino)-4H-2,3-dihydrobenzothiopyran; and
(2'S)-2,2-dimethyl-5-hydroxy-7-pentyl-4-(2'-acetoxypropylimino)-4H-2,3-dihydrobenzothiopyran.

EXAMPLE 10

A solution of 2,2,7-trimethyl-5-hydroxy-4-(2'-hydroxypropylimino)-4H-2,3-dihydrobenzopyran (269 mg, 0.001 mol) in anhydrous dichloromethane (5 ml) was dropped into a slurry of pyridinium chlorochromate (258 mg, 0.0012 mol) in 5 ml of dichloromethane. After 3 hrs. at room temperature, ethyl ether (10 ml) was added, the mixture was filtered and evaporated. Column chromatography on silica gel gave 130 mg of 2,2,7-trimethyl-5-hydroxy-4-(2'-oxopropylimino)-4H-2,3-dihydrobenzopyran, as a glassy solid.

The following compounds as pure enantiomers and as a racemic mixture thereof were analogously prepared:
2,2-dimethyl-5-hydroxy-7-pentyl-4-(2'-oxopropylimino)-4H-2,3-dihydrobenzopyran;
2,2-dimethyl-5-hydroxy-7-(1',2'-dimethylheptyl)-4-(2'-oxopropylimino)-4H-2,3-dihydrobenzopyran; and
2,2-dimethyl-5-hydroxy-7-(1',1'-dimethylheptyl)-4-(2'-oxopropylimino)-4H-2,3-dihydrobenzopyran.

EXAMPLE 11

Tablets, each weighing 150 mg and containing 50 mg of the active substance were manufactured as follows:

Composition (for 10,000 tablets)

(2'R)-2,2-dimethyl-5-hydroxy-7-pentyl-4-(2'-hydroxypropylimino)-4H-2,3-dihydrobenzopyran: 500 g
Lactose: 710 g
Corn starch: 237.5 g
Talc powder: 37.5 g
Magnesium stearate: 15 g
(2'R)-2,2-dimethyl-5-hydroxy-7-pentyl-4-(2'-hydroxypropylimino)-4H-2,3-dihydrobenzopyran, lactose and a half of the corn starch were mixed; the mixture was then forced through a sieve of 0.5 mm openings. Corn starch (18 g) was suspended in warm water (180 ml). The resulting paste was used to granulate the powder. The granules were dried, comminuted on a sieve of sieve size 1.4 mm, then the remaining quantity of starch, talc and magnesium stearate was added, carefully mixed, and processed into tablets using punches of 8 mm diameter.

What we claim is:
1. A compound having the following general formula (I)

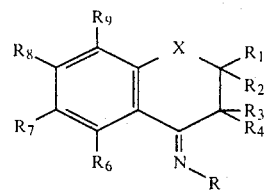

wherein
X is —O— or —S—;
each of $R_1$, $R_2$ and $R_3$, being the same or different, is hydrogen, $C_1$-$C_{10}$ alkyl or phenyl; or $R_1$ and $R_2$, taken together, form a $C_5$-$C_7$ cycloalkyl ring;
$R_4$ is hydrogen or $C_1$-$C_6$ alkyl;
$R_6$ is —$OR_{10}$ or —$SR_{10}$, wherein $R_{10}$ is hydrogen or $C_1$-$C_6$ alkyl;
$R_5$ is $C_1$-$C_{10}$ alkyl, $C_2$-$C_{10}$ alkenyl or $C_3$-$C_7$ cycloalkyl, wherein the alkyl, alkenyl and cycloalkyl groups are unsubstituted or substituted by one or more substituents chosen from the group consisting of halogen, oxo, —$OR_{10}$, —$SR_{10}$, —$COR_{10}$, —$OCOR_{10}$, —$COOR_{10}$ and

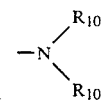

wherein each of the groups $R_{10}$, being the same or different, is as defined above;
one of $R_7$, $R_8$ and $R_9$ is $C_1$-$C_{12}$ alkyl and the others, which may be the same or different, are hydrogen or $C_1$-$C_{12}$ alkyl, and the pharmaceutically acceptable salts thereof.

2. A compound having the general formula (I) reported in claim 1, wherein
X is —O— or —S—;
$R_1$ is hydrogen, $C_1$-$C_7$ alkyl or phenyl;
$R_2$ is hydrogen or $C_1$-$C_4$ alkyl; or $R_1$ and $R_2$, taken together, form a $C_5$-$C_6$ cycloalkyl ring;
each of $R_3$ and $R_4$ is, independently, hydrogen or $C_1$-$C_4$ alkyl;
$R_5$ is $C_2$-$C_6$ alkenyl or $C_1$-$C_5$ alkyl, wherein the alkyl group is unsubstituted or substituted by one or two substituents chosen from oxo, —$OR'_{10}$, —$SR'_{10}$, —$COOR'_{10}$

and —$OCOR'_{10}$, wherein each of $R'_{10}$ is independently hydrogen or $C_1$-$C_4$ alkyl; or $R_5$ is $C_3$-$C_6$ cycloalkyl;
$R_6$ is hydroxy, mercapto, $C_1$-$C_2$ alkoxy or $C_1$-$C_2$ alkylthio; one of $R_7$, $R_8$ and $R_9$ is $C_4$-$C_{12}$ alkyl and the others, which may be the same or different, are hydrogen or $C_1$-$C_{12}$ alkyl, and the pharmaceutically acceptable salts thereof.

3. A compound having the general formula (I) reported in claim 1, wherein

X is —O— or —S—;
$R_1$ is hydrogen or $C_1$-$C_6$ alkyl;
each of $R_2$, $R_3$ and $R_4$ is independently, hydrogen or $C_1$-$C_4$ alkyl;
$R_5$ is allyl, cyclopentyl, cyclohexyl or a radical chosen from 2-hydroxy-propyl-, 2-acetoxy-propyl-, 2-propionyloxy-propyl-, 2-hydroxy-ethyl-, 2-ethoxycarbonyl-ethyl-, 2-hydroxy-2-methyl-propyl-, 2-hydroxy-1-methyl-ethyl-, 2-hydroxy-butyl-, 1-hydroxy-methyl-propyl-, 2-oxo-propyl-, 2-amino-propyl-, 2-dimethylamino-ethyl-, 2-methylamino-ethyl-, 2-mercapto-propyl-, 3-carboxy-propyl-, 2-methoxy-ethyl- and 2-mercapto-ethyl;
$R_6$ is hydroxy, mercapto, $C_1$-$C_2$ alkoxy or $C_1$-$C_2$ alkylthio; one of $R_7$, $R_8$ and $R_9$ is $C_5$-$C_{10}$ alkyl and the others are hydrogen, and the pharmaceutically acceptable salts thereof.

4. 2,2-dimethyl-5-hydroxy-7-pentyl-4-(2'-hydroxypropylimino)-4H-2,3-dihydrobenzopyran and its pharmaceutically acceptable salts.

5. (2'R)-2,2-dimethyl-5-hydroxy-7-pentyl-4-(2'-hydroxypropylimino)-4H-2,3-dihydrobenzopyran and its pharmaceutically acceptable salts.

6. (2'S)-2,2-dimethyl-5-hydroxy-7-pentyl-4-(2'-hydroxypropylimino)-4H-2,3-dihydrobenzopyran and its pharmaceutically acceptable salts.

7. A compound selected from the group consisting of:
2,2-dimethyl-5-hydroxy-7-(1',2'-dimethylheptyl-4-(2'-hydroxypropylimino)-4H-2,3-dihydrobenzopyran;
2,2-dimethyl-5-hydroxy-7-pentyl-4-(2'-acetoxypropylimino)-4H-2,3-dihydrobenzopyran;
2,2-dimethyl-5-hydroxy-7-(1',1'-dimethylheptyl)-4-(2'-hydroxypropylimino)-4H-2,3-dihydrobenzopyran;
2,2-dimethyl-5-hydroxy-7-pentyl-4-(2'-mercaptopropylimino)-4H-2,3-dihydrobenzopyran;
2,2-dimethyl-5-mercapto-7-pentyl-4-(2'-hydroxypropylimino)-4H-2,3-dihydrobenzopyran;
5-hydroxy-7-pentyl-4-(2'-hydroxypropylimino)-4H-2,3-dihydrobenzopyran;
5-hydroxy-7-pentyl-4-(2'-hydroxypropylimino)-4H-2,3-dihydrobenzothiopyran;
2,2-dimethyl-5-hydroxy-7-pentyl-4-(2'-dimethylaminoethylimino)-4H-2,3-dihydrobenzothiopyran; and
2,2-dimethyl-5-hydroxy-7-pentyl-4-allylimino-4H-2,3-dihydrobenzothiopyran;
and the pharmaceutically acceptable salts thereof.

8. 2,2-dimethyl-5-hydroxy-7-pentyl-4-(2'-hydroxypropylimino)-4H-2,3-dihydrobenzothiopyran, and its pharmaceutically acceptable salts.

9. (2'R)-2,2-dimethyl-5-hydroxy-7-pentyl-4-(2'-hydroxypropylimino)-4H-2,3-dihydrobenzothiopyran, and its pharmaceutically acceptable salts.

10. (2'S)-2,2-dimethyl-5-hydroxy-7-pentyl-4-(2'-hydroxypropylimino)-4H-2,3-dihydrobenzothiopyran, and its pharmaceutically acceptable salts.

11. A pharmaceutical composition containing a suitable carrier and/or diluent and, as an active principle, a compound of formula (I), according to claim 1, or a pharmaceutically acceptable salt thereof.

12. A method for sedating a patient comprising administering to the patient a sedative effective amount of the compound according to claim 1.

13. A method of preventing convulsions in a patient comprising administering to the patient an anti-convulsive effective amount of the compound according to claim 1.

14. A method for tranquilizing a patient comprising administering to the patient a tranquilizing effective amount of the compound according to claim 1.

15. A method of inducing sleep in a patient comprising administering to the patient a sleep inducing effective amount of the compound according to claim 1.

* * * * *

UNITED STATES PATENT AND TRADEMARK OFFICE
CERTIFICATE OF CORRECTION

PATENT NO. : 4,497,820

DATED : February 5, 1985

INVENTOR(S) : MERLINI et al

It is certified that error appears in the above-identified patent and that said Letters Patent is hereby corrected as shown below:

Column 1 line 20 and column 14 line 16 formula (I): "R" substituent is to be amended to read --$R_5$--

Column 3 line 38 and column 15 line 35, at the end of these lines delete "dimethylheptyl-4-(2'-" and replace by --dimethylheptyl)-4-(2'- --

Column 9 line 47 delete and replace by --2-methyl-5-hydroxy-7-pentyl-4-(2'-hydroxy- --

Signed and Sealed this

Third Day of December 1985

[SEAL]

Attest:

DONALD J. QUIGG

Attesting Officer     Commissioner of Patents and Trademarks